United States Patent [19]

Bailey et al.

[11] Patent Number: 4,860,598
[45] Date of Patent: Aug. 29, 1989

[54] AIR-STREAM SAMPLING DEVICE

[75] Inventors: Christian E. Bailey, Port Deposit, Md.; John J. Bowser, Wilmington, Del.

[73] Assignee: W. L. Gore & Associates, Inc., Newark, Del.

[21] Appl. No.: 716,361

[22] Filed: Mar. 26, 1985

[51] Int. Cl.$^4$ .......................... G01N 1/22; G01N 1/20
[52] U.S. Cl. ................................ 73/863.33; 73/863.51
[58] Field of Search ........... 73/861.66, 863.31, 863.33, 73/863.51, 863.58, 864.73, 863.81, 28, 865.5; 356/335–343, 438, 439; 364/555; 377/10–12

[56] References Cited

U.S. PATENT DOCUMENTS

| | | | |
|---|---|---|---|
| 3,777,571 | 12/1973 | Jaeger | 73/863.81 |
| 3,842,679 | 10/1974 | Baun et al. | 73/863.58 |
| 3,981,193 | 9/1976 | Goulet | 73/861.66 |
| 4,061,036 | 12/1977 | Le Gille | 73/863.31 |
| 4,602,514 | 7/1986 | Kurrle et al. | 73/861.66 |
| 4,615,224 | 10/1986 | Smith et al. | 73/863.33 |
| 4,624,146 | 11/1986 | Nakagawa | 73/861.66 |

OTHER PUBLICATIONS

"LEEM Vessel Internal Collection & Distribution Systems", 4 page advertisement by LEEM Filtration Products, Inc.; by Mar. 25, 1985.

Primary Examiner—Tom Noland
Attorney, Agent, or Firm—Mortenson-Uebler

[57] ABSTRACT

A device for drawing a small representative sample of air from a laminar flow air stream, such as that flowing through a clean room, is provided, which comprises a gridwork of evenly-spaced tubes having regularly spaced orifices to sample representatively a laminar flow stream of air to determine the number of particles therein. The gridwork of tubes is sized and configured to leave the laminar flow of the air stream substantially undisturbed.

7 Claims, 1 Drawing Sheet

U.S. Patent  Aug. 29, 1989  4,860,598
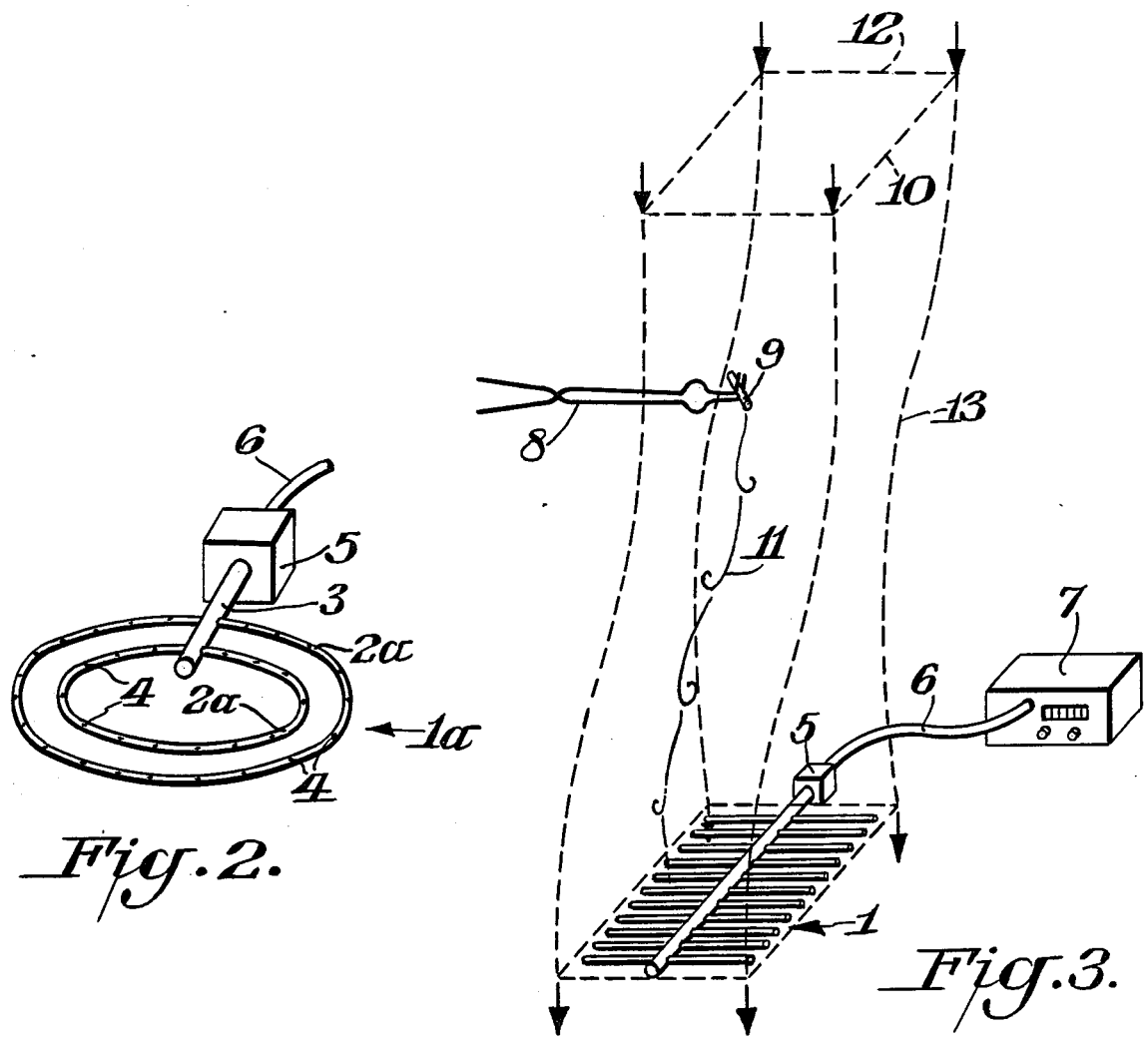
Fig. 2.
Fig. 3.
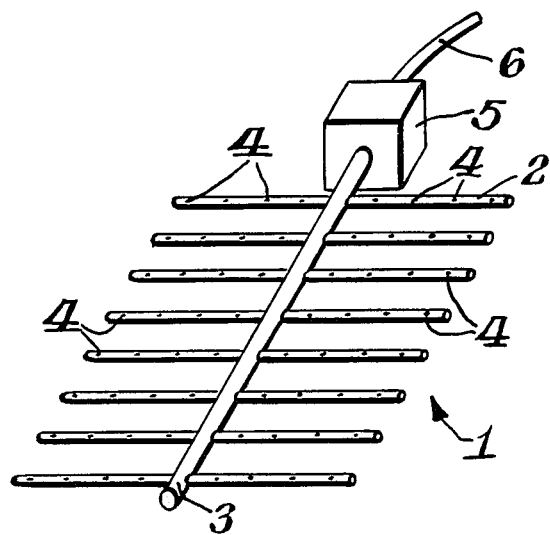
Fig. 1.

AIR-STREAM SAMPLING DEVICE

BACKGROUND OF THE INVENTION

Field of the Invention

This invention relates to sampling of a flowing stream of air or gas for aerosol particles. The invention relates more particularly to a device for drawing a small representative sample of air from a large-volume stream of laminar flow air in a clean room.

In clean rooms, for example, of the type useful for manufacture or handling of sterile pharmaceutical or pure chemical materials or for manufacture of sensitive optical or electronic parts or devices, it is required that the air be sampled periodically and routinely to establish the level of cleanliness in the room or at specified work stations or locations therein or when a particulate leak is suspected. A common practice is to draw this air sample from a length of tubing, the entrance of which is located generally in the area of interest. However, it is recognized that particles in laminar flow air streams in clean rooms move only along paths originating at the source of the particles and follow air flow stream lines through the clean room. Thus, a sampling tube collects a particle only if the entrance to the tube is placed directly in the path of the particle.

To solve this problem, more complex methods have been used. One process draws subsequent samples at a multitude of points, analyzes or counts these, and averages or combines the resulting data, but this method is difficult to execute and is time consuming and, thus, can be expensive. Additionally, phenomena which one may wish to measure occur over a shorter time period than this method requires, and therefore cannot be accurately represented by this technique. Another process uses a network of single sampling tubes interconnected by valves to allow selection of any one of the separate corresponding sampling locations at any one time. This is cumbersome and still difficult and time consuming to use. A process of drawing a number of air samples simultaneously, analyzing these simultaneously by means of an equal number of analyzing instruments, e.g. particle counters, and combining the resulting data is much faster than the methods above, but very cumbersome and possibly quite costly. One type of sampling device, specifically one type of an impactor, appears to draw and combine air samples simultaneously at a multitude of locations, the entrances to which are distributed over part of its exterior. This design is not, however, intended to achieve representative sampling of a body of air moving in laminar flow. The solid and continuous shape of the impactor causes the laminar flow of air to be diverted and to part around the device. Thus, the air brought to the multiplicity of sampling locations is representative only of that air in the streamline in front of the device which parts as it passes around the device.

Accordingly, it is an object of the present invention to provide a device for drawing a single continuous representative sample from a body of air moving in laminar flow for analysis or counting of the particles therein.

SUMMARY OF THE INVENTION

A device is provided for sampling a laminar flow air stream to be monitored for the presence of particles comprising at least one sampling tube having a multiplicity of regularly spaced orifices therein, the orifices being of substantially smaller size than the interior bore of the sampling tube, and each orifice being capable of drawing equally from the air stream, the sampling tube being sized to minimize any diversion of the air stream from its original path, means for drawing a sample of air from the air stream through the orifices, and means to analyze the particles in the sample drawn from the air stream. Preferably the device comprises a planar gridwork of a plurality of sampling tubes evenly spaced apart, each sampling tube connected to a single outlet tube, the gridwork having a size and configuration selected to minimize any diversion of the air stream from its original path. The orifices in the tubes can be of equal size or, in the gridwork, the orifices in the tubes can be of progressively increasing size the farther they are disposed from the single outlet tube of the gridwork. The means to analayze the particles in the sample can be by counting them or by using an optical particle analyzer, or by other conventional means. The gridwork of evenly-spaced interconnected tubes preferably has one exit for the sampled air, and the gridwork approximates in size the cross section of the air stream being sampled.

BRIEF DESCRIPTION OF THE DRAWINGS

FIG. 1 is a perspective of a preferred rectangular form of the planar gridwork device of the invention.

FIG. 2 is an alternative double ring form of the device.

FIG. 3 illustrates a method for using the inventive device to analyze for the particles contained in a body of moving air of specified dimensions which will pass by the device in a specified length of time.

DETAILED DESCRIPTION OF THE PREFERRED EMBODIMENTS

The objects of the invention are accomplished by placing into a cross section of the laminar flow air stream of interest a planar gridwork 1, as shown in FIGS. 1 and 3, of interconnected hollow tubes 2 and 3, each of the smaller tubes 2 having a number of small orifices 4 along its length such that, as a group, all the orifices 4 in all the tubes 2 constitute a matrix of entrances to the interior of the tubes 2 of the gridwork 1. From the single outlet 3 for the gridwork is drawn the representative sample. The matrix of orifices 4 is regular, evenly spaced, the orifices 4 all being of the same size. The cross-sectional area of any tube 2 must be greater than the sum of the cross-sectional areas of all orifices which feed it. Thus, nearly all of the pressure drop associated with drawing a sample through the device is owing to the orifices and the flow of air is substantially equal through each orifice. Therefore, the sample is equally representative of all locations across the span of the gridwork and of the cross section of the laminar flow body of air being analyzed. In an alternate embodiment, the orifices in the tubes 2 are of progressively increasing size the farther they are disposed from the single outlet tube 3 of the gridwork 1. In both embodiments, sample tubes should not be so long that unacceptable particle loss occurs during the transport of aerosol.

The tubes 2 and 3 of which the planar gridwork 1 is constructed are of small diameter in relation to the spaces between them and the gridwork is generally of light and open form such that a body of air in laminar flow, such as that present in a clean room, is not substantially diverted around the area occupied by the gridwork, but passes through and by it largely undisturbed and remains in laminar flow as before such that a cross section, rather than the streamline leading to the parting of the airflow, is represented. The importance of the form not disturbing the air flow is primarily that the sample is not made unrepresentative, rather than that the flow downstream maintains the same laminar character. The area of the gridwork device chosen is the same as that of a cross section of the area of interest to be sampled and is placed downstream of any suspected or indicated known source of particles and mounted in place by means of accessory holding and fastening devices and equipment which will not interfere with the laminar flow air stream around the device. The single representative sample is drawn from the common outletof the gridwork and analyzed for particles by any of the common ways or devices, such as by a particle counter, an optical particle analyzer, condensation nucleus counter, mobility analyzer, aerodynamic sizer, diffusion battery, electrical size analyzer, electrostatic sampler, piezoelectric microbalance, aerosol electrometer, impactor, etc.

FIG. 2 shows an alternative embodiment of a planar gridwork 1a of interconnected hollow circular tubes 2a having a number of orifices 4, similar to the orifices 4 in gridwork 1, such that, as a group, all the orifices 4 in the tubes 2a constitute a matrix of entrances to the interior of the tubes 2a of the circular gridwork 1a. Common outlet tube 3, fitting 5, and tube 6 are shown for completeness.

FIG. 3 depicts a perspective view of an aerosol sampling experiment to illustrate how the device of the invention is to be used in which a burning cigarette 9 is held by a pair of tongs 8 upstream of the gridwork device 1 in the moving body of air whose boundaries are shown by dotted lines such as 10, 12, and 13. The tobacco smoke aerosol particles are released in the laminar flowing body of air illustrated as circumscribed by the dotted lines and carried through the area occupied by the gridwork device 1, where a sample is taken, which passes through the connecting fitting 5 and tube 6 to the analyzer 7 where the particles are counted.

The preferred material comprising the tubes of the gridwork is stainless steel welded into the gridwork of the invention. A preferred means to provide the orifices is by having them drilled by means of a laser beam. Other methods for providing the orifices may be used so long as they can provide smooth, uniform, usually circular, holes in the tubes.

Other materials may be utilized as tubes to form the gridwork of the device of the invention so long as the gridwork can be made of minimum bulkiness or tubing diameter so as to retain the laminar flow characteristic of the air stream being sampled by the device. Other metals than stainless steel or stiff tubes of other materials compatible with the aerosol may be alternatively utilized. Other gridwork shapes than those illustrated may be used so long as they approximate in shape the cross section of air stream of interest, and do not substantially interfere with the laminar flow of air.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

We claim:

1. A device for sampling a small representative fraction of a laminar flow air stream to be monitored for the presence of particles in a clean room environment, said device comprising:
    (a) a gridwork of a plurality of sampling tubes evenly spaced apart, each said sampling tube connected to a single outlet tube, said gridwork having a size and configuration selected to minimize any diversion of said air stream from its original path, said sampling tubes having a multiplicity of regularly spaced orifices therein, said orifices being of substantially smaller size than the interior bores of said sampling tubes, and each orifice being capable of drawing equally from said air stream;
    (b) means for drawing a sample of air from said air stream through said orifices; and
    (c) means to analyze the particles in said sample drawn from said air stream.

2. A device of claim 1 wherein said gridwork is planar.

3. A device of claim 1, wherein the orifices in said tubes are of equal size.

4. A device of claim 1, wherein the orifices in said tubes are of progressively increasing size the farther they are disposed from the single outlet tube of said gridwork.

5. A device of claim 1, wherein the means to analyze the particles in the sample is by counting them.

6. A device of claim 1, wherein the means to analyze the particles in the sample is an optical particle analyzer.

7. A device of claim 1, where said gridwork of evenly-spaced interconnected tubes has one exit for the sampled air and the said gridwork approximates in size the cross section of the air stream being sampled.

* * * * *